(12) United States Patent
Gruzdowich et al.

(10) Patent No.: US 7,171,266 B2
(45) Date of Patent: Jan. 30, 2007

(54) ELECTRO-ACUPUNCTURE DEVICE WITH STIMULATION ELECTRODE ASSEMBLY

(75) Inventors: Gregory J. Gruzdowich, Carlsbad, CA (US); Thomas L. Grey, Carlsbad, CA (US); Robert J. Duffy, Carlsbad, CA (US); Hogar Tait, Carlsbad, CA (US); Thomas L. Mann, Carlsbad, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/441,803

(22) Filed: May 19, 2003

(65) Prior Publication Data

US 2003/0195585 A1    Oct. 16, 2003

Related U.S. Application Data

(63) Continuation of application No. 09/722,258, filed on Nov. 24, 2000, now Pat. No. 6,567,695.

(51) Int. Cl.
*A61N 1/04* (2006.01)
(52) U.S. Cl. .................... 607/2; 607/115; 128/907
(58) Field of Classification Search .............. 128/907; 439/909; 600/372, 382, 384, 386, 390, 395–397; 607/1–2, 44–46, 58, 115, 148, 149
See application file for complete search history.

(56) References Cited

U.S. PATENT DOCUMENTS 4,834,103 A * 5/1989 Heath ........................ 600/372
4,981,146 A   1/1991 Bertolucci .................. 128/802
5,224,928 A * 7/1993 Sibalis et al. ................ 604/20
5,441,520 A * 8/1995 Olsen et al. .................. 607/6
5,456,710 A * 10/1995 Gadsby ..................... 607/142
5,749,913 A * 5/1998 Cole ........................... 607/59
5,978,701 A * 11/1999 Johnson et al. .............. 604/20
6,032,064 A * 2/2000 Devlin et al. ............... 600/383
6,076,018 A   6/2000 Sturman ..................... 607/72

FOREIGN PATENT DOCUMENTS

| FR | 2646779 | 5/1989 |
|---|---|---|
| FR | 2646779 | * 11/1990 |
| WO | 91/17737 | 11/1991 |
| WO | WO 91/17737 | * 11/1991 |

* cited by examiner

Primary Examiner—Robert E. Pezzuto
Assistant Examiner—Kristen Mullen
(74) Attorney, Agent, or Firm—David L. Weinstein

(57) ABSTRACT

An electro-acupuncture device for controlling nausea. The device includes a base unit which is includes a wrist-watch like housing, circuitry for generating electro-acupuncture stimulus disposed within the housing, and a strap for securing the housing to the wrist. The base unit has a standardized construction. The device also includes a releasably attachable electrode assembly. The electrode assembly attaches to the base unit of the device. The electrode assembly includes a pair of electrodes and connectors for connecting the electrodes to the circuitry of the base unit. The output of the device is dependent upon the circuitry of the electrode assembly. Thus various electrode assemblies can be made. The circuitry of the base unit modifies the output of the device depending upon which electrode assembly is attached to the base unit.

2 Claims, 11 Drawing Sheets

ELECTRO-ACUPUNCTURE DEVICE WITH STIMULATION ELECTRODE ASSEMBLY

This application is a continuation of U.S. application Ser. No. 09/722,258, filed Nov. 24, 2000, now U.S. Pat. No. 6,567,695.

FIELD OF THE INVENTIONS

The methods and devices described below relate to the field of electro-acupuncture and non-invasive stimulation of nerves.

BACKGROUND OF THE INVENTIONS

We have developed an electro-acupuncture device which has proven effective for the control of nausea and vomiting. The device, marketed under the trademark Relief-Band®, is worn on the wrist like a wristwatch, with a watch-like housing which is positioned on the underside of the wrist. The housing has two electrodes on the inside face (the face in contact with the wrist when secured to the wrist), a battery and circuitry inside the housing, and control buttons on the outer face. A patient suffering from nausea or vomiting (from seasickness, morning sickness, chemotherapy, or anesthesia) can strap the device onto their wrist and turn it on. When turned on, the device emits an electrical stimulation pulse over the P6 acupuncture point (corresponding to the superficial course of the meridian nerve through the wrist). Within several minutes, most patients experience a substantial relief of nausea. The device uses non-invasive nerve stimulation whereby electricity is passed through two electrodes to stimulate nerves located on the ventral side of the wrist (this anatomical position is sometimes referred to as the palmar side of the wrist). The treatment provided by the device is sometimes referred to as electro-acupuncture, which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. It is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices. The device is described in Bertolucci, *Nausea Control Device*, U.S. Pat. No. 4,981,146 (Jan. 1, 1991).

Previously, we have provided devices in several models, each providing a different strength of stimulation deemed appropriate for particular patients and indications. We have also marketed a version of the device which included circuitry and operator controls which allowed the patient to select from a wide range of power setting and stimulation patterns. Currently, we are marketing over-the-counter devices and prescription devices. Both the over-the-counter device and the prescription are provided in embodiments in which the device is disposable (the batteries cannot be replaced after depletion) and in which the device is reusable, (the batteries may be replaced indefinitely). In each of these versions, we have provided complete circuitry, power supply, and electrodes in each device manufactured. Thus, for each version of the device, different circuitry had to be provided. The devices and methods described below provide for easier manufacturing of a line of devices with different characteristics. In each of our electro-acupuncture products, the stimulation and effect are greatly enhanced if the patient applies a gel to the skin before strapping the device onto the wrist. This gel serves as an impedance matching layer between the electrodes and the skin, greatly enhancing the effect of the device and lowering the power requirements for the device. As a replacement for the gel, we have developed a gel coating for the electrodes. This coating comprises a hydrogel film which adheres to the electrodes and can be applied to the electrodes during manufacture. Providing the gel during manufacture enhances effectiveness of the device since it eliminates the possibility that some users will omit the application of gel, either through forgetfulness or ignorance of need to use it. A current limitation on the installed hydrogel film is its short lifespan. The films that are currently available last only a few days. While this is acceptable for some temporary indications and applications, such as seasickness, it is undesirable for chronic applications such as morning sickness and chemotherapy induced nausea. Our solution is to provide the device in modular form, with the watch-like housing manufactured in one unit and the electrodes manufactured as an attachable or insertable part which can be readily replaced by the patient.

SUMMARY

The devices and methods described below provide for improved usability and control of electro-acupuncture devices in particular, and electrical stimulation devices in general. The electro-acupuncture device includes a pair of electrodes connected to control circuitry and a battery. The control circuitry operates to draw power from the battery and generate electro-acupuncture stimulation pulses to the electrodes. The control circuitry is housed in a housing, which, for application of stimulus to the P6 point on the wrist, is preferably a wrist-watch like housing that may be strapped on the wrist with watch band or the like. The electrodes are mounted to the inner face of the housing, so that they rest over the P6 point when the housing is worn on the inside of the wrist. The electrodes are provided on an assembly which is separable from the housing. The assembly may then be used to control the operation of the device, to provide for several modes of therapy, by inclusion of configuration elements which contain unique parameters or digital information which as accessed by the control circuit when the electrode assembly is secured to the base unit. The electrode assembly becomes a "smart electrode," capable of carrying information usable by the control circuit to configure the overall device. Additionally, the impedance matching gel that is required for optimal performance of the device can be applied during manufacture (rather than during use), since it may be inexpensively replaced with a new electrode assembly.

DETAILED DESCRIPTION OF THE INVENTIONS

Figure 1:
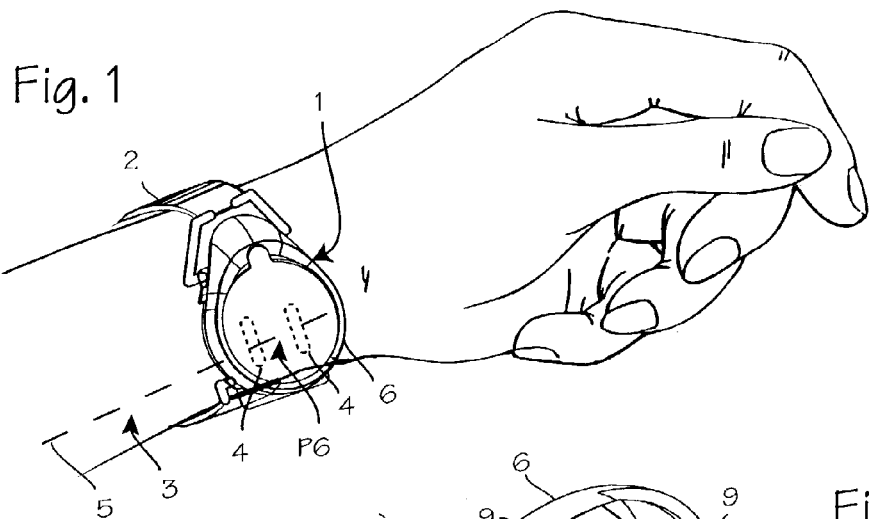
FIG. 1 the device in use on the wrist of the patient.

FIG. 1 illustrates the device in use on the wrist of the patient. The non-invasive nerve stimulation device 1 is secured with a strap 2 to the ventral side of the wrist 3 such that the pair of electrodes 4 were disposed over the median nerve 5 (indicated by the phantom line) and in contact with the skin in the vicinity of the P6 acupuncture point. The electrodes are on the underside of the housing 6, the required battery and control electronics are housed within the housing, and input mechanisms (push buttons, dials, and the like) are located on the outer face of the housing. For electro-acupuncture applications on the wrist, two electrodes 4 are provided, and these two electrodes are place on the assembly so that, when applied to the wrist, the electrodes are disposed over the P6 point and oriented so that the long axis of each is perpendicular to the median nerve while the pair is oriented along the length of the median nerve.

Figure 2:
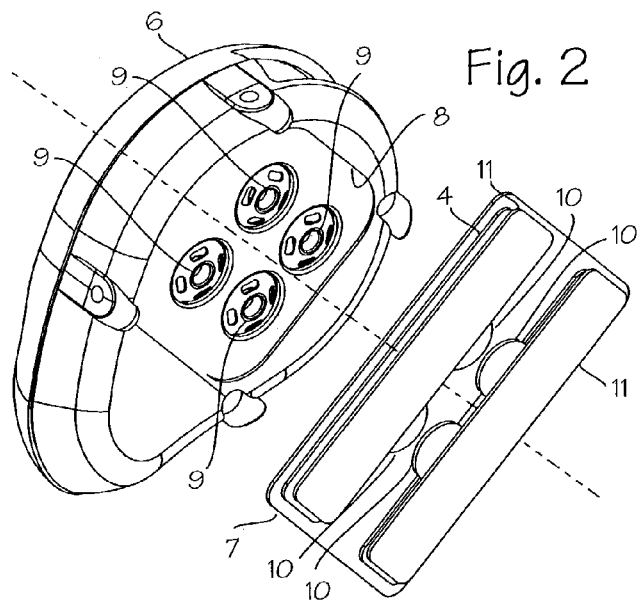
FIG. 2 is a view of the bottom of the device showing the placement of the electrode assembly on the bottom of the housing.

As shown in FIG. 2, the nerve stimulation device is formed in two parts, including the housing 6 and an electrode assembly 7. The electrode assembly is releasably attachable to the housing so that it may be easily yet securely attached and removed by a user. The underside of the housing 6 is fitted with a receiving aperture 8 for receiving the electrode assembly. Several releasable fasteners are provided in the form of simple snap sockets 9, which are preferably comprised of electrically conductive material so that they may also be used to electrically connect the pulse generation circuitry within the housing to the electrodes on the electrode assembly. The sockets receive snap studs shown in FIG. 3. The electrode assembly includes the electrodes 4 on the bottom of the assembly, opposite the bottom of the housing. The snap stud bases 10 can be seen from the underside of the electrode assembly, and these support the studs shown in FIG. 3. Each electrode is covered by an impedance matching film 11. The film is comprised of a hydrogel with suitable impedance, adhesive properties, and material strength and softness. The hydrogel is applied during manufacture and covered with a protective sheet of plastic which is removed by the user after attaching the electrode assembly to the housing. (Impedance matching can also be accomplished with separately applied gel).

Figure 3:
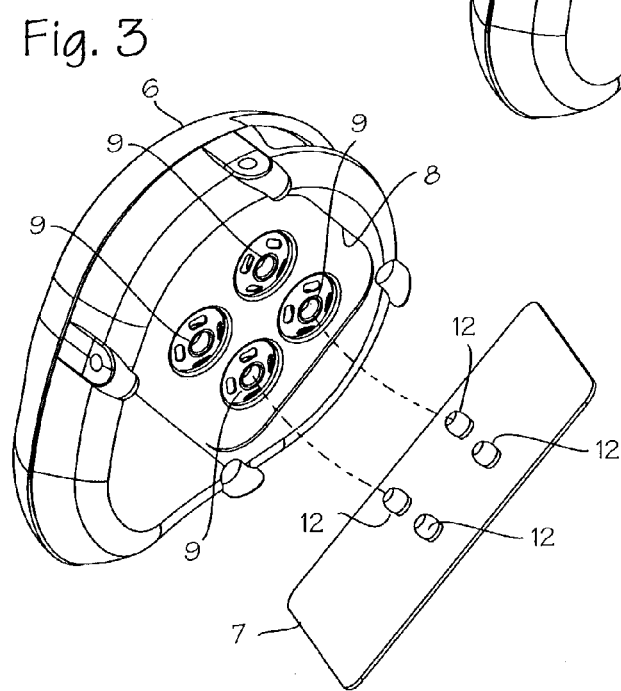
FIG. 3 is a view of the bottom of the device showing the snap fittings used to secure the electrode assembly on the bottom of the housing.

FIG. 3 shows the top of the electrode assembly 7 in position opposite the bottom of the housing 6, illustrating that electrode assembly includes one or more protrusions 12 on the upper side of the assembly which are keyed to the shape of the sockets on the underside of the housing. These protrusions may be the studs of a typical fabric snap fastener, and are preferably comprised of electrically conductive material so that they may also be used to electrically connect the pulse generation circuitry within the housing to the electrodes on the electrode assembly. While four snap connectors are illustrated, more or less may be used depending on the number of connections required for a particular circuit. Any male/female connector or multi-pin connector may be used in place of the snaps illustrated. Also, additional connectors may be used to establish the connections illustrated in the following schematics while using the snaps or other fasteners merely for attaching the electrode assembly to the housing.

Figure 4:
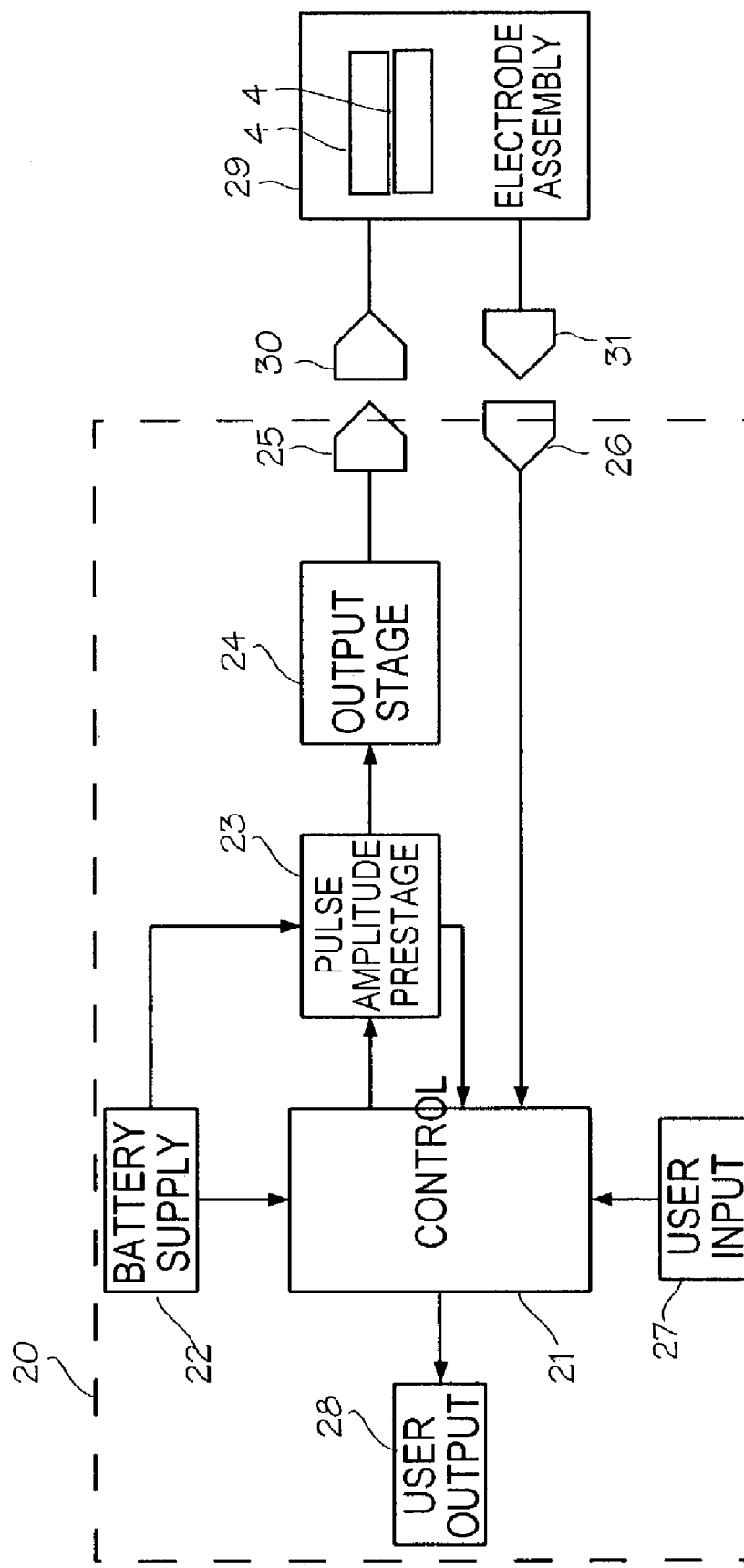
FIG. 4 is a block diagram of the system.

FIG. 4 is a block diagram of the circuitry in the housing and the electrode assembly. The housing is represented by item 20, and houses the control circuitry 21, battery 22, pulse amplitude pre-stage 23 and the output stage 24 which provides electrical stimulation output to the electrodes through output connector 25, and a sensing connector 26 which provides input to the control circuit. The user controls are represented by the user input 27 and the indicator lights are represented by user output 28. The electrode assembly is represented by item 29, and includes an output receiving connector 30 and a sensing connector 31 and the two electrodes 4. The sensing connectors 26 and 31 are releasably electrically connected, as through pronged connectors, pin & socket connectors, metal snaps (as illustrated in FIGS. 2 and 3) or other standard releasable electrical connectors. The output connectors 25 and 30 are releasably electrically connected, also through pronged connectors, pin & socket connectors, metal snaps or other standard releasable electrical connectors. The sensing connectors and output connectors may be ganged in the same connector housing, with pins connected as required to interconnect the appropriate components on each side of the connector. Custom connectors may also be used, and may be fabricated from conductive carbon rubber or other suitable material.

Figure 5:
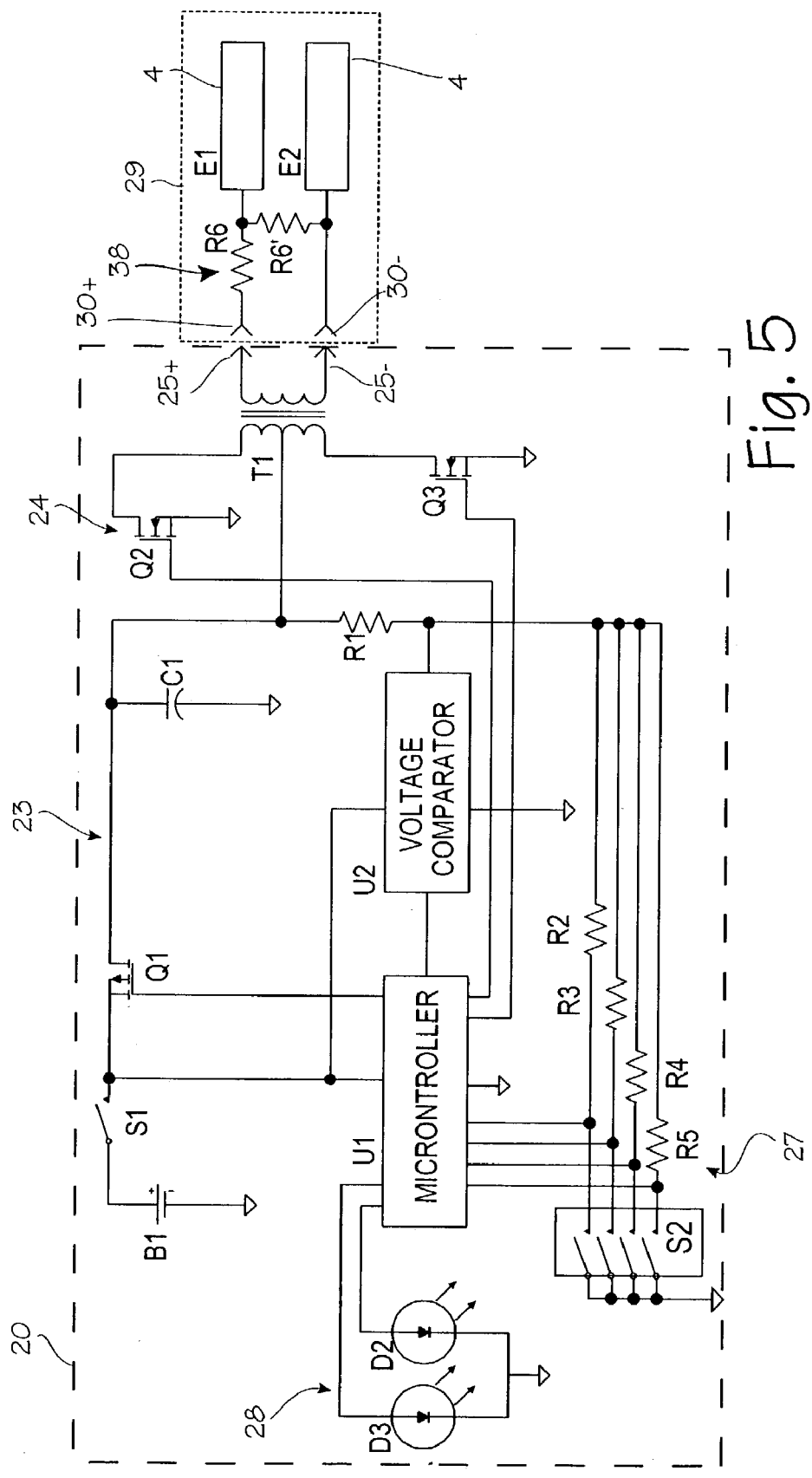
FIG. 5 is a schematic diagram of the circuitry of a basic electro-acupuncture system capable of changing the output amplitude range through a simple resistor divider network in the disposable electrode.

FIG. 5 is a schematic of a basic form of the system. This system will provide pulsed stimulation output of varying power depending on the particular electrode assembly used in the system. FIG. 5 shows details of the stimulation circuit, including the switch 52 and resistors R2, R3, R4 and R5 which make up the user input 27, the diodes D2 and D3 which make up the user output 28, the microcontroller U1, the battery B1 and switch S1 which connects the battery to the remainder of the circuit, the transistor Q1, capacitor C1, resistor R1 and voltage comparator U2 that make up the pre-stage 23, and the transistors Q2 and Q3 and transformer T1 which make up the output stage 24. The transformer T1 serves to boost the voltage of the stimulation pulses to therapeutic levels. The control circuit, drawing power from the battery, operates other components of the system to generate stimulation pulses of predetermined pulse length, amplitude, and pulse pattern. The voltage comparator operates to provide feedback for generating selected intensities. Operation of these elements is described in detail in our co-pending U.S. Pat. No. 6,076,018, incorporated herein by reference.

As shown in FIG. 5, the electrode assembly 29 includes the two electrodes 4, and a configuration element 38. The configuration element may be any component, feature or circuit layout that imparts any electronically identifiable parameter to the electrode assembly (which may or may not be in circuit or integrally connected to the electrodes). In FIG. 5, the configuration element is a resistor divider (R6 and R6') connected to the output stage. (The configuration element may simply be a resistor in series with the output stage (R6) or in parallel with the output stage (R6').) The output connectors are separated into connectors 30+ and 30− on the electrode assembly and connectors 25+ and 25− on the housing, and the sensing connectors are combined with these connectors since the configuration element is part of the output circuitry. The ratio of the resistor divider is chosen to effect the desired output power and voltage of the electrodes 4. (The resistance ratio chosen for the resistor divider may be any value, so long as it is predetermined in the sense that it is selected in coordination with programming and design of the control circuitry, or it is known and the control circuitry can be designed accordingly to recognize the parameter.)

The maximum strength possible from any given output at the output connectors 30+ and 30− is achieved when the resistance of R6 is zero (a short). Lower strength is achieved by adjusting the resistor divider ratio relative to the load resistance (or impedance). Other impedance control elements (e.g. a capacitor or an inductor may be used. In this embodiment, the base unit determines the output range (e.g., up to 35 mA) in software/hardware, and the configuration element in the disposable electrode assembly shifts this range (e.g., limiting the maximum actual output to a lower value such as 5 mA to 25 mA). Several desired output levels may be effected with several different electrode assemblies incorporating resistors of different values.

Figure 6:
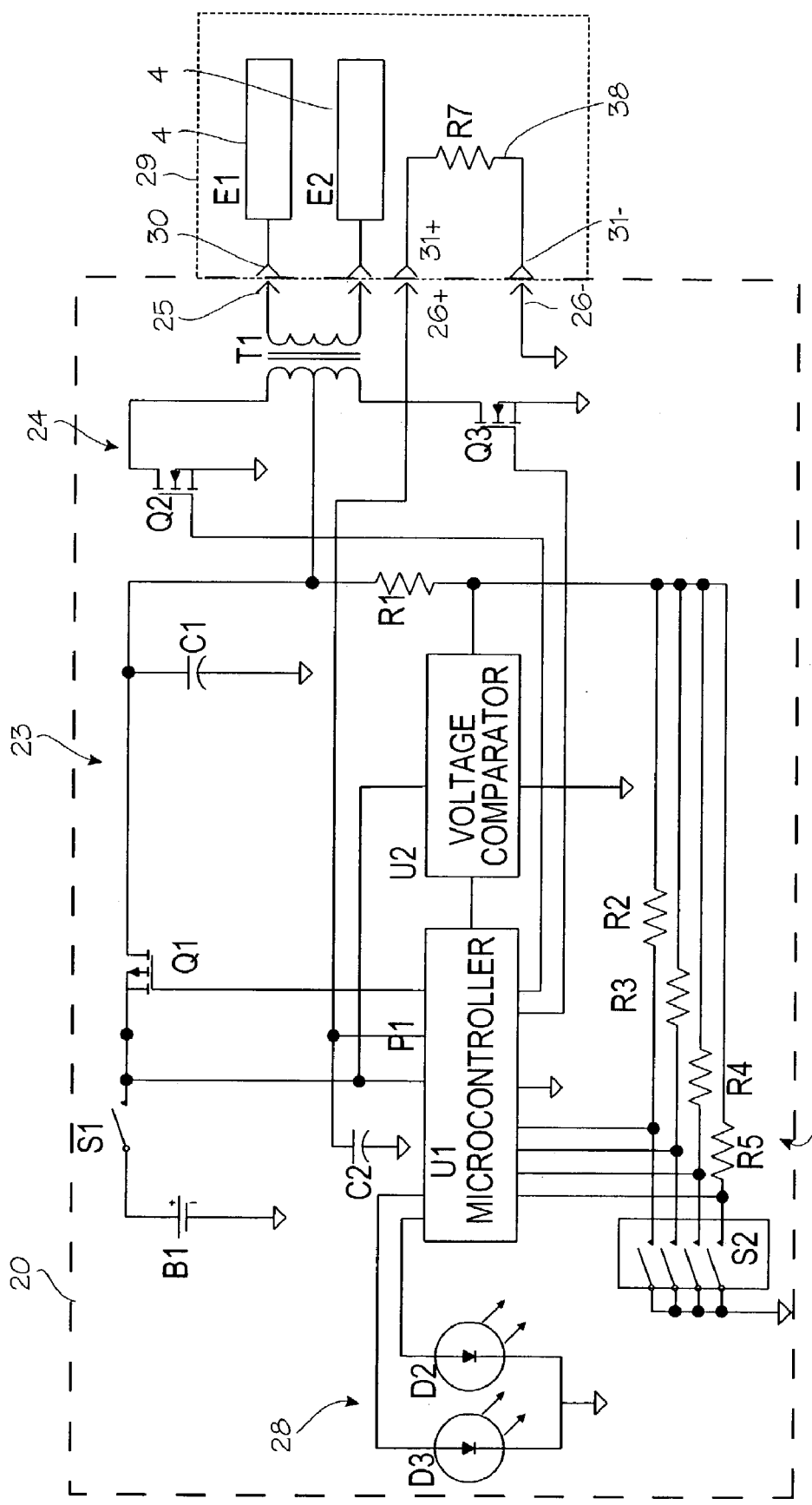
FIG. 6 is a schematic diagram of the circuitry of the electro-acupuncture system capable of a number of different configuration modes set by the value of a resistor within the system.

In FIG. 6, a more versatile form of the smart electrode assembly is demonstrated that is better suited to constant current output stages where load resistance has little or no effect. Here, the configuration element is a resistor connected to the microcontroller via a separate set of connectors represented by 26+ and 26− and 31+ and 31− in the electrode assembly 29 and base unit 20. In this Figure, microcontroller input line P1 is normally connected to capacitor C2. The configuration element 38 is provided in the form of resistor R7, and the microcontroller and capacitor C2 are used to determine the presence or absence of R7. When the electrode assembly is connected to the base unit, the resistor R7 forms an RC timing circuit in conjunction with the capacitor C2 in the housing. The micro-controller input line P1 is connected to a parallel RC circuit whose resistance and capacitance are known, therefore, the RC time constant is known. Otherwise line P1 is connected to an RC circuit where R is infinite and the time constant is quite long. The microcontroller software sets P1 to a high voltage to charge the capacitor, then sets P1 to a high impedance. After a predetermined time, the software checks P1 again to determine if the capacitor voltage is low. If the resistor is in place, the voltage is low; if not, the voltage should still be high (that is, the time constant is long). Thus, the micro-controller can determine the electrical parameter (resistance of R7) by determining the time constant of the RC timing circuit created upon connection of the electrode assembly to the housing and the resultant placement of the resistor R7 into the circuit. (In these examples, the RC timing circuit is established upon connection of the base and the electrode assembly, but the capacitor C2 may be placed on the electrode assembly, with provision of a connection to P1 through the connectors, so that the micro-controller may sense the RC constant of an RC timing circuit housed entirely within the electrode assembly.)

Upon determination of the resistance value of R7 or the time constant of the resultant RC timing circuit, the microcontroller then sets the output range according to a predetermined schedule which is programmed into the microcontroller. For example, the microcontroller and electrode combination may be set up so that upon sensing the presence of resistor R7, the microcontroller will produce a pulsed stimulation output in a first predetermined output range, while upon failure to sense resistor R7 within the electrode assembly the microcontroller will produce a pulsed stimulation output in a second predetermined output range. Different values for the resistance of R7 may be used to provide multiple configuration inputs corresponding to multiple output options. For example, one electrode assembly may use a certain resistance providing a shorter time constant $T_1$, while a second electrode assembly may use a different resistance resulting in a longer time constant $T_2$. The microcontroller may then be configured to check the capacitor voltage at $T_1$. I the voltage is still high, then the microcontroller will check again at $T_2$ for the presence of the second assembly. The number of different potential values for R7 will depend on the number of desired output options, and the resolution of the microcontroller (its ability to discriminate between sensed time constants).

While FIG. 6 is described with the resistor R7 placed on the electrode assembly and the capacitor C2 installed in the housing, the two components may be swapped. Placement of capacitor C2 on the electrode assembly, and varying its capacitance according to the desired behavior of the assembled device (together with appropriate programming of the microcontroller) can be used as an alternate implementation of the circuit shown in FIG. 6. Thus it can be appreciated that the configuration element may be most any electronic component that be use analyzed by the control circuitry.

Figure 7:
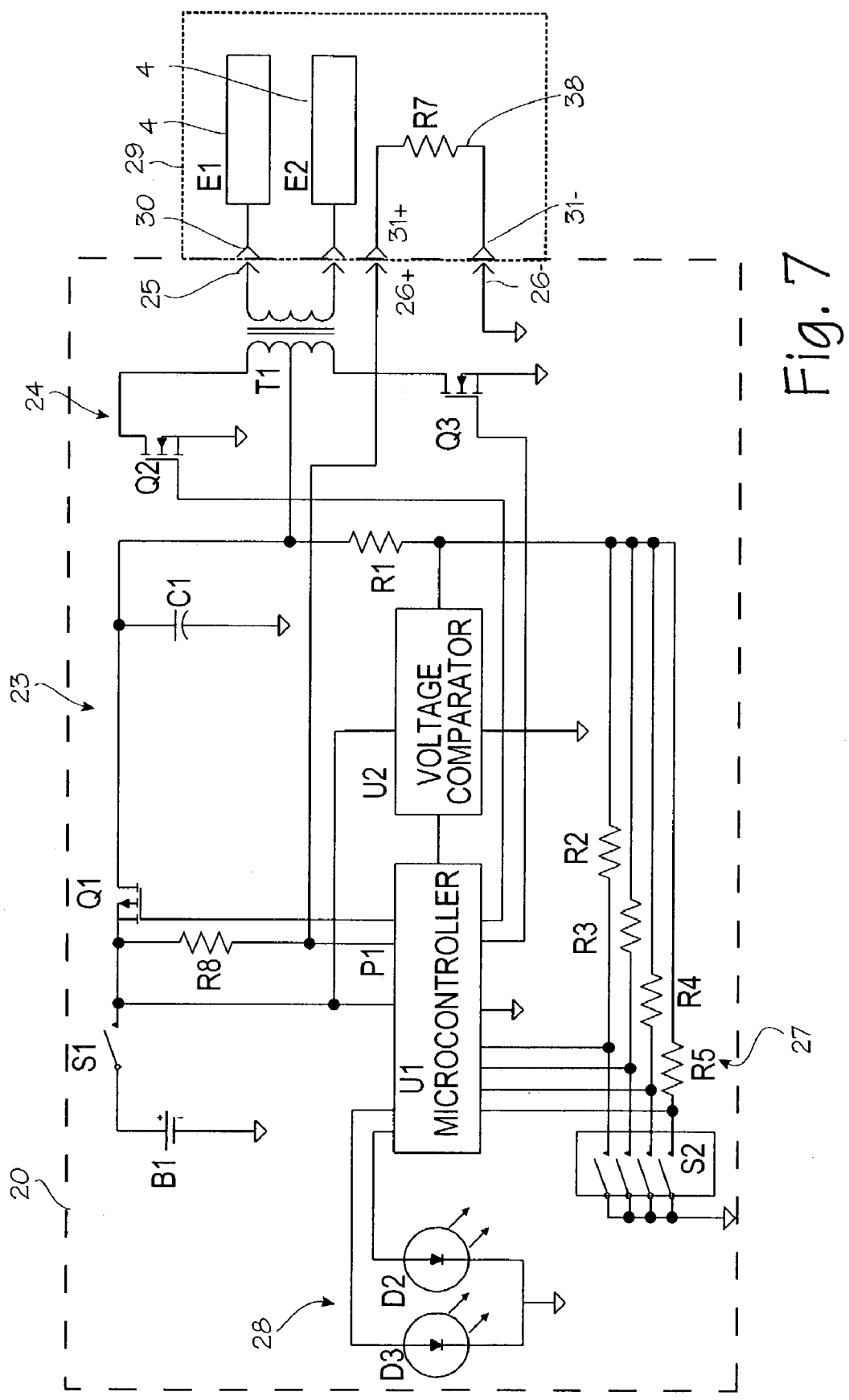
FIG. 7 is a schematic diagram of the circuitry of the electro-acupuncture system capable of a number of different configuration modes set by the value of a resistor within the system.

In FIG. 7, a variation of the electrode assembly and control circuitry of FIG. 6 is demonstrated. In FIG. 7, the configuration element 38 is a pull-down resistor R7 connected to the micro-controller via a separate set of connectors 26 and 31 in the base unit 20 and electrode assembly 29. In this Figure, micro-controller input line P1 is normally connected to a high voltage through pull-up resistor R8. When the electrode assembly is connected, micro-controller input line P1 is pulled down to ground through resistor R7 if it is in place. Otherwise line PI remains in a high voltage state. The micro-controller then sets the output range according to a predetermined schedule which is programmed into the micro-controller. For example, the micro-controller and electrode combination may be set up so that upon sensing the presence of resistor R7, the micro-controller will produce a pulsed stimulation output in a first predetermined output range, while upon failure to sense resistor R7 within the electrode assembly the micro-controller will produce a pulsed stimulation output in a second predetermined output range. The system of FIG. 7 is essentially a 1-bit configuration port with two possible states (1, 0). However, different values of a resistor will provide different voltage values at line P1, which can be sensed with resolution sufficient to discern the presence of resistors of various resistance. Accordingly, line P1 can be configured as an analog to digital (A/D) converter to allow the micro-controller software to read the voltage and set operation performance parameters accordingly. The number of possible configurations is then limited only by the resolution of the A/D converter. A separate A/D converter circuit could also be implemented, but is less desirable for producing a highly miniaturized device. Additionally, the addition of another pull-up resistor and another set of connections to the micro-controller, along with another configuration resistor in the electrode assembly, results in a 2-bit port (00, 01, 10, 11) providing four different output ranges or other operational performance configurations. Addition of a third set of pull-up resistor and configuration resistor connected to a third I/O port on the micro-controller can be used in this hardwired bit code scheme achieves a 3-bit port providing eight different output ranges.

Figure 8:
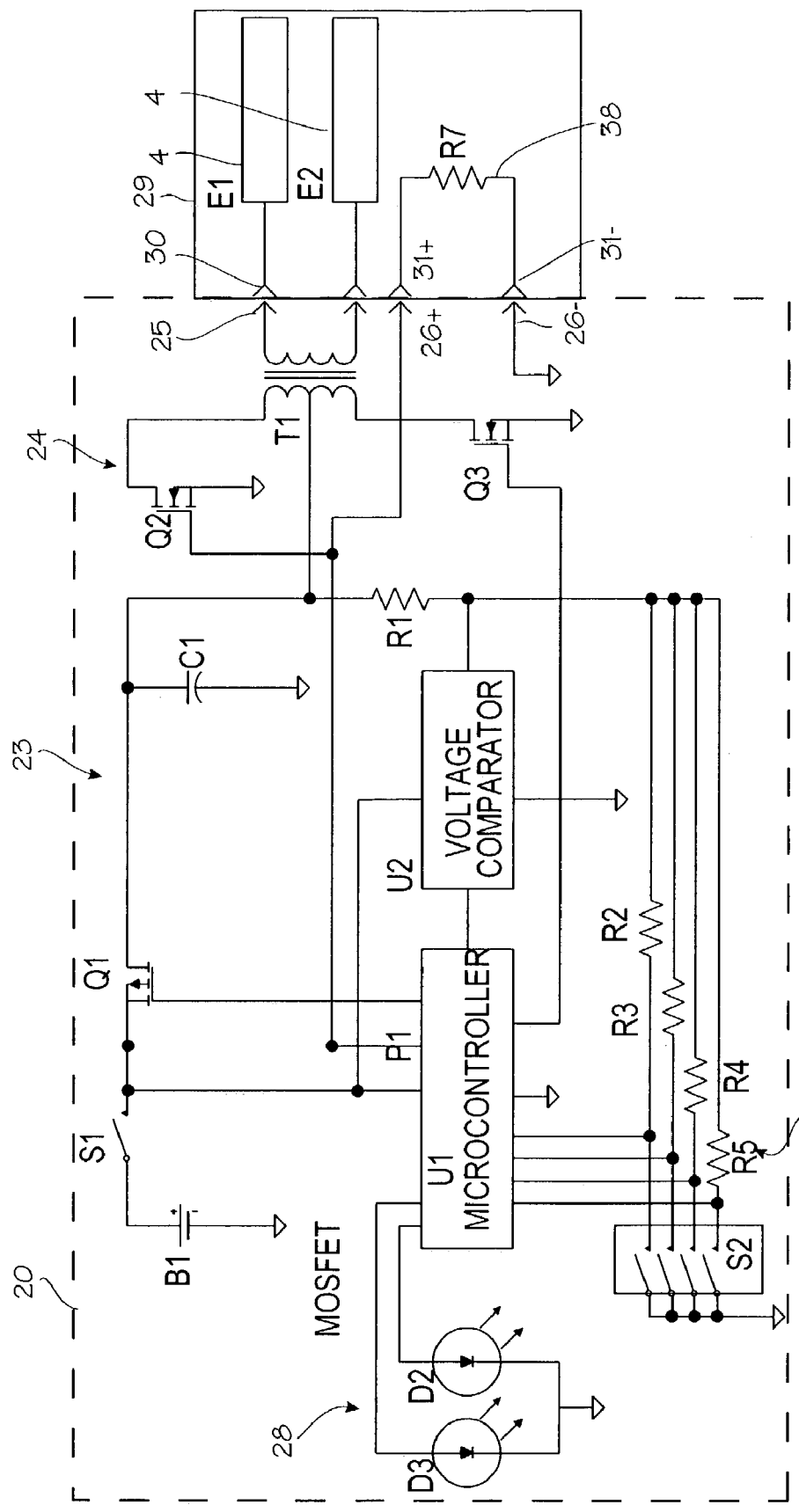
FIG. 8 is a schematic diagram of the circuitry of the electro-acupuncture system capable of a number of different configuration modes set by the measure of the time for discharge of capacitance from an element in the circuit, which is dependent on a configuration element in the electrode assembly.

In place of the capacitor C2 of FIG. 6, it is possible to use any device with capacitance. For example, P1 may be connected to drive the gate of an N-channel MOSFET type transistor whose source is connected to ground. This is illustrated in FIG. 8, with MOSFET or transistor Q2 (which is already in place in the output circuitry) placed in the configuration circuit with the gate of the MOSFET connected to ground through the configuration element R7 which is located in the electrode assembly 7. The resistor R7 in this case is preferably a high value resistor on the order of 1 MOhm.

While the normal function of PI (in this embodiment) is to control the MOSFET for discharging stimulation pulses to the transformer T1, the provision the large resistor from gate to source allows operation of P1 as a 1-bit port for determining circuit configuration. The micro-controller charges the stray capacitance between the gate and source, and also monitors the state of P1. During startup, the micro-controller outputs a short high voltage on the I/O pin P1, which will charge the node capacitance of the gate, and then the micro-controller will change the I/O pin to a high impedance. The micro-controller will then count the number of clock cycles until a low or zero voltage is read on the I/O pin P1. If resistor R7 is not in place, between the gate and ground, the time for the voltage to drop to ground will be long, and dependent on the leakage current of the MOSFET. The controlling software will be able to count a high number of cycles or loops before decay of the voltage. If the resistor R7 is in the circuit between the gate and ground, the time for decay of the voltage on the I/O pin P1 will be short. The decay time will be related to the value of R7 and the node capacitance. In prototype circuits, the decay or discharge to zero voltage at the I/O pin requires a relatively long period of 90 msec without the resistor R7 in place, and a relatively short period of 360 µsec with a 1 MOhm resistor in the R7 position. The micro-controller is then programmed to interpret a short decay time as an indication that the user has inserted an electrode assembly having a resistor in the R7 position, and, conversely, to interpret a long decay time as an indication that the user has inserted an electrode assembly without a resistor in the R7 position. In this manner, the micro-controller can determine the presence or absence of the configuration element. The micro-controller is additionally programmed to operate in different modes depending on the presence or absence of the configuration element.

Figure 9:
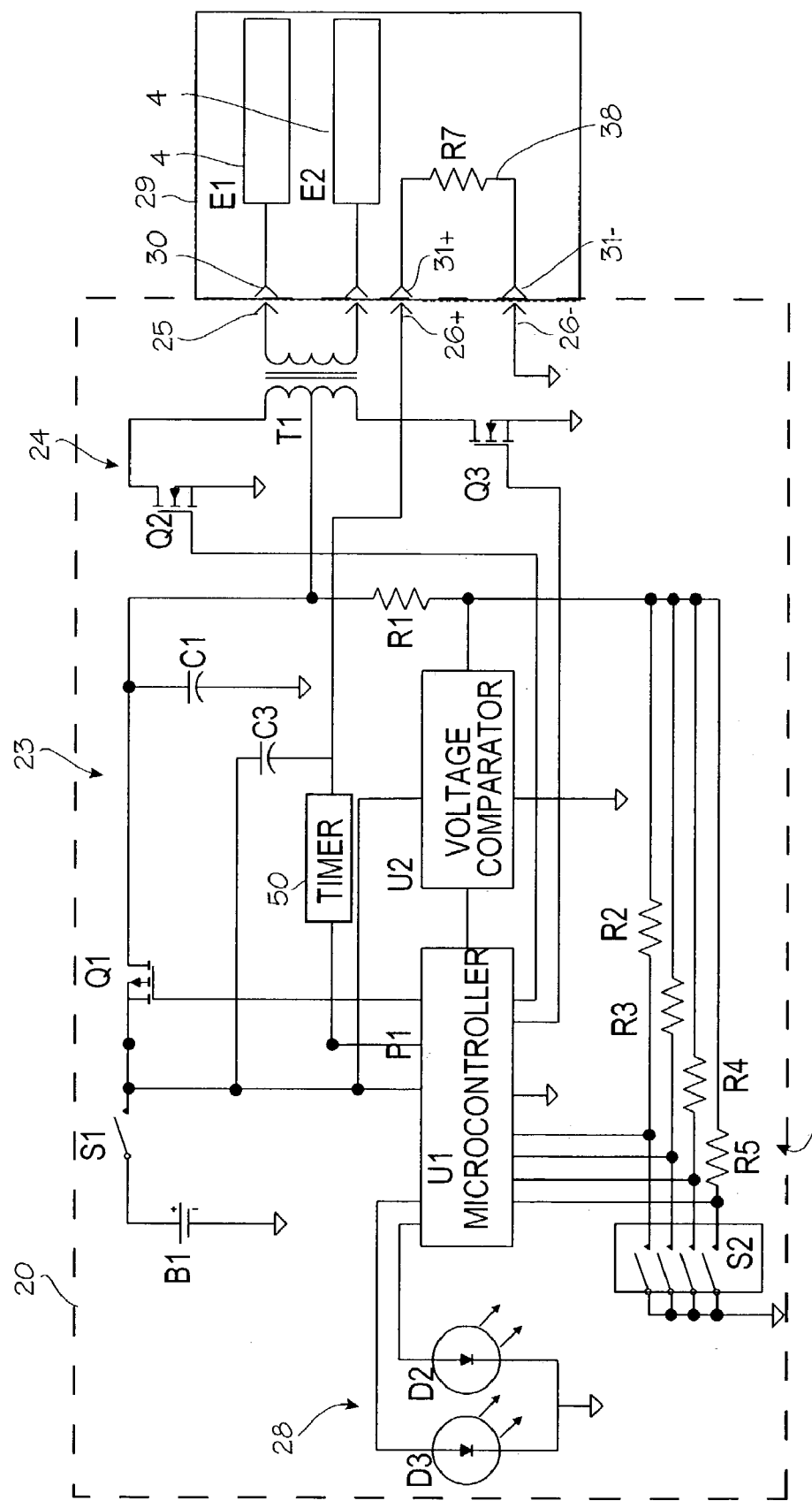
FIG. 9 is a schematic diagram of the circuitry of the electro-acupuncture system capable of a number of different configuration modes set by alteration of frequency of a voltage controlled oscillator by the configuration element.

FIG. 9 illustrates a different implementation in the base unit of FIG. 6 which allows the R7 component to be used in cooperation with a simple timing circuit, e.g., based on the ubiquitous 555 timer set in free running mode (or a voltage controlled oscillator), that is then interfaced to the micro-controller. Different values of R7 will change the output frequency of the timer 50. This output frequency is read by the microcontroller from P1, thereby allowing the micro-controller to determine the required operation performance parameters by the particular output frequency produced by a particular value of R7. In this example, a capacitor in the timing circuit could replace the resistor in the electrode assembly.

Figure 10:
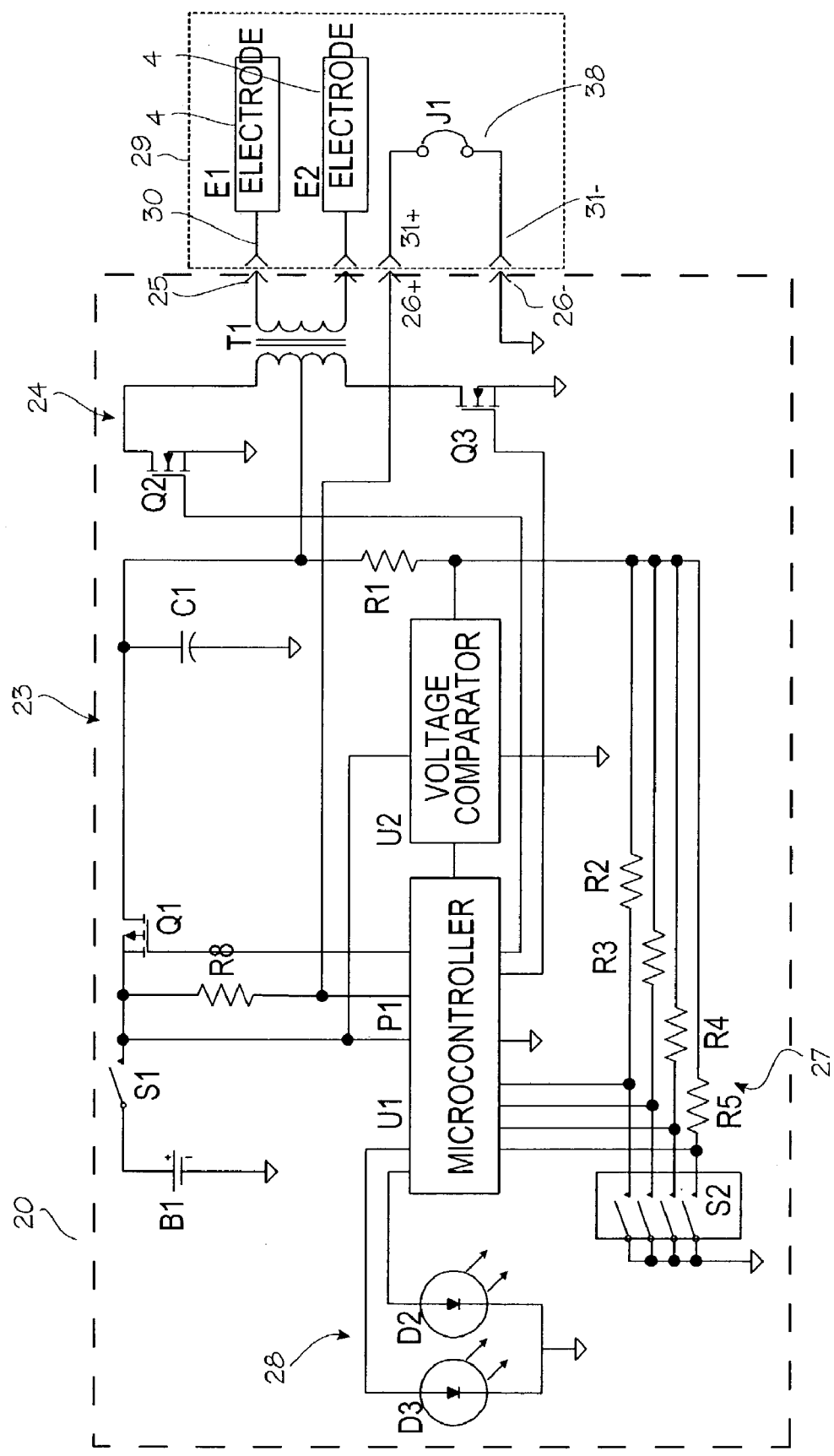
FIG. 10 is a schematic diagram of the circuitry of the electro-acupuncture system capable of implementing a simple on/off configuration wherein the micro-controller software merely detects the presence of absence of the disposable electrode that has a simple shorting element.

Another variation of the hardwired bit code scheme is shown in FIG. 10 wherein resistor R7 is replace by a simple jumper. Resistor R8 is used to pull-up micro-controller line P1 and a simple jumper J1 is used to bridge the sensing connectors 26+ and 26−. Again, the presence or absence of this jumper determines the operational performance parameters as determined in software. As discussed above in relation to FIG. 7, multiple jumpers and microcontroller lines can be used to implement multi-bit ports. Also, elements can be combined. For example, the jumper J1 of FIG. 10 can be combined with the resistor divider of FIG. 5 such that the jumper acts as an enable/disable element in which the devices does not turn on unless the jumper is properly connected, while a resistor or divider connected through another set of connectors to a separate I/O port of the microcontroller is used to select the appropriate operating behavior.

Figure 11:
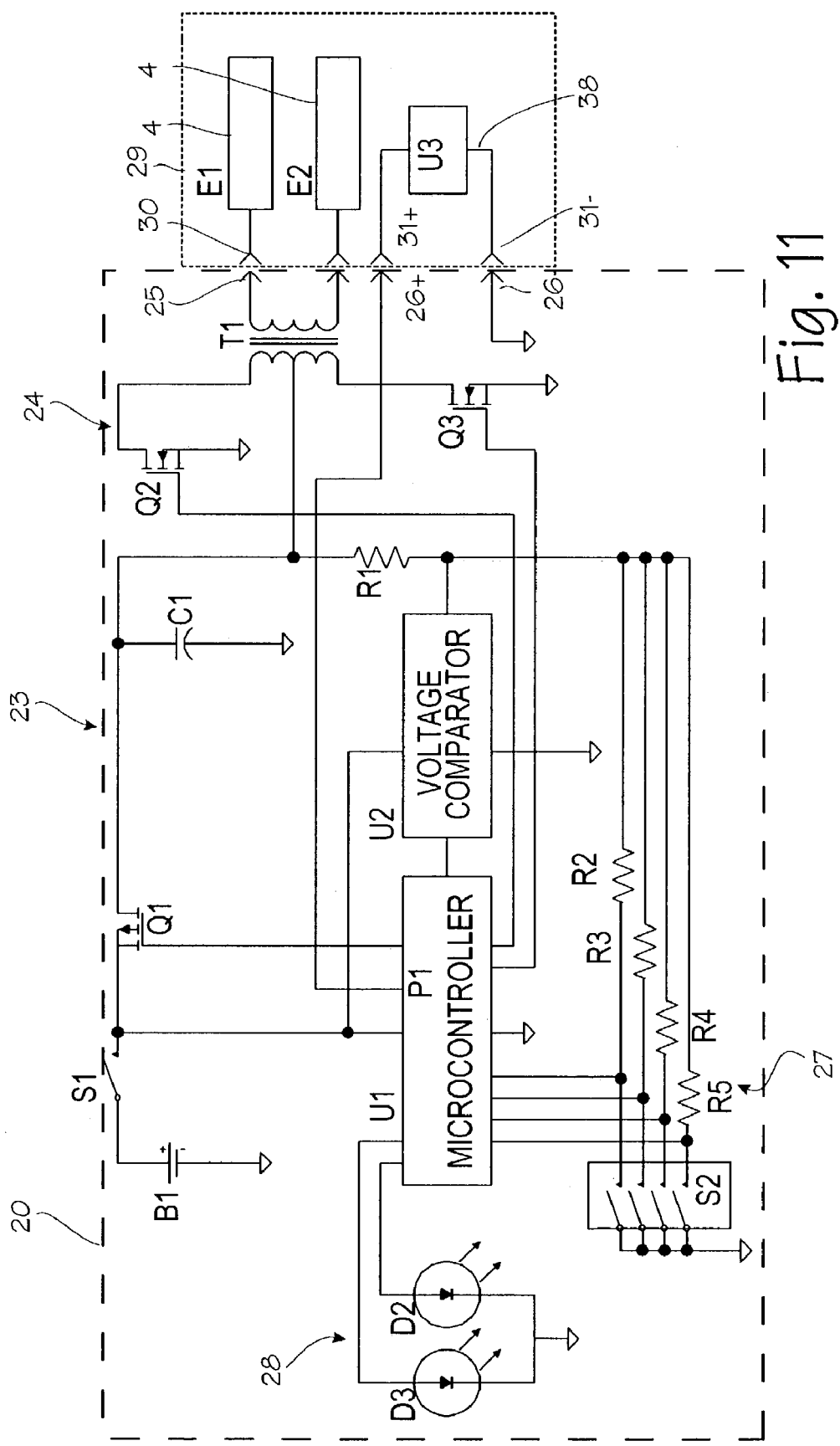
FIG. 11 is a schematic diagram of the circuitry of the system in which the electrode assembly includes an EPROM.

FIG. 11 demonstrates a more sophisticated implementation using a 1-bit serial programmable memory device (U3) (e.g., PROM) or similar device such as the Dallas Semiconductor DS2401 Silicon Serial Number device, which requires only two connections to a microcontroller. More physical connectors between the electrode assembly and the base unit would accommodate other ROM bit storage devices requiring more interface signals to the microcontroller. In the schematic of FIG. 11, the ROM is programmed with information that defines the required operational performance parameters. This information may be any digital information which the micro-controller is programmed to interpret and may be in any form which the micro-controller is capable of reading.

A wide variety of parameters can be programmed for use with either a single base unit or a family of base units (e.g., prescription parameters versus over-the-counter parameters, nausea of pregnancy parameters versus motion sickness parameters, etc.). For example, our current over the counter product is limited to output of 35 mA and the prescription product is limited to 40 mA. Rather than require users to purchase an entire new unit for every occasional need, the user may purchase one non-disposable base unit then purchase electrode assemblies which will permit a limited period of use. Also, rather than require users to purchase an entire new unit for treatment of various conditions (motion sickness and chemotherapy, for example), the user may purchase one non-disposable base unit usable for either condition, then be prescribed electrode assemblies which will permit the higher strength output for the duration of the chemotherapy. These methods and devices allow a single base unit to be marketed in various countries with different regulatory requirements for electro-acupuncture devices. For example, under current United States regulations, there is no restriction on how long a stimulating device can operate, but under current Japanese regulations, stimulating devices are required to automatically shut off after twenty minutes of continuous use. The same-base unit may be manufactured for sale in both countries, with a controller set to limit operations depending on a sensed configuration element in the electrode assembly. The relevant regulations can be met by providing different electrodes assemblies with configuration elements which are used in combination with the controller in the base unit to limit operation as required.

Output ranges can also be selected using the configuration element. A first output range can be a standard output suitable for over the counter distribution, useful for conditions such as seasickness. The second output range can be a high strength output suitable for treatment of chemotherapy nausea or post operative anesthesia nausea, suitable for distribution only by prescription. Thus, two or more distinct devices can be manufactured with identical components except for the electrode assembly, eliminating the burden of producing multiple base units. Additionally, prescription and over the counter distribution may be controlled by controlling the disposable electrodes rather than controlling the entire device. Additionally, the system allows a single user to purchase a single base unit and use it for either prescription use or over the counter use, rather than having to buy two entire systems.

Figure 12:
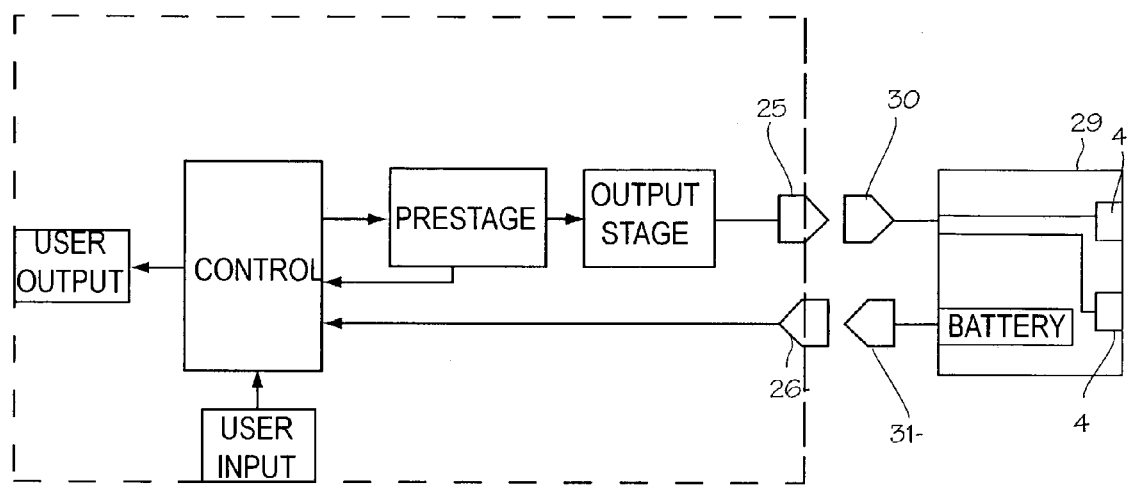
FIG. 12 is a schematic diagram of the circuitry of the system in which the battery is carried on the electrode assembly.

In addition the control of dosage, the electrode assembly can be used to prevent activation of the control circuitry to generate stimulation pulses unless an electrode assembly in place. In the simplest form, this system may be configured by placing the battery on the electrode assembly. This configuration is shown in FIG. 12. The electrode assembly 29 of FIG. 12 is similar to the electrode assemblies described previously, but is also holds the battery 22. Preferably, the microcontroller 21 is designed and programmed to awaken to a ready condition similar to the sleep condition or energy saver condition used for large electronics, and begin generating stimulation pulses when the user uses the operator input to turn the device on. In this embodiment, the user replaces the electrode assembly when the battery is depleted.

The releasably attached electrode, as described above, allows a clean and easy way to make sure that users have a properly applied layer of gel which is required for making proper electrical contact between the electrodes and the skin, without permitting any degree of user mistake or oversight to interfere with effectiveness. The advantage in this regard is that users will not deem the device ineffective and then seek otherwise unnecessary drug treatment for the nausea they suffer. In this embodiment, the user replaces the electrode assembly when the gel layer deteriorates.

Figure 13:
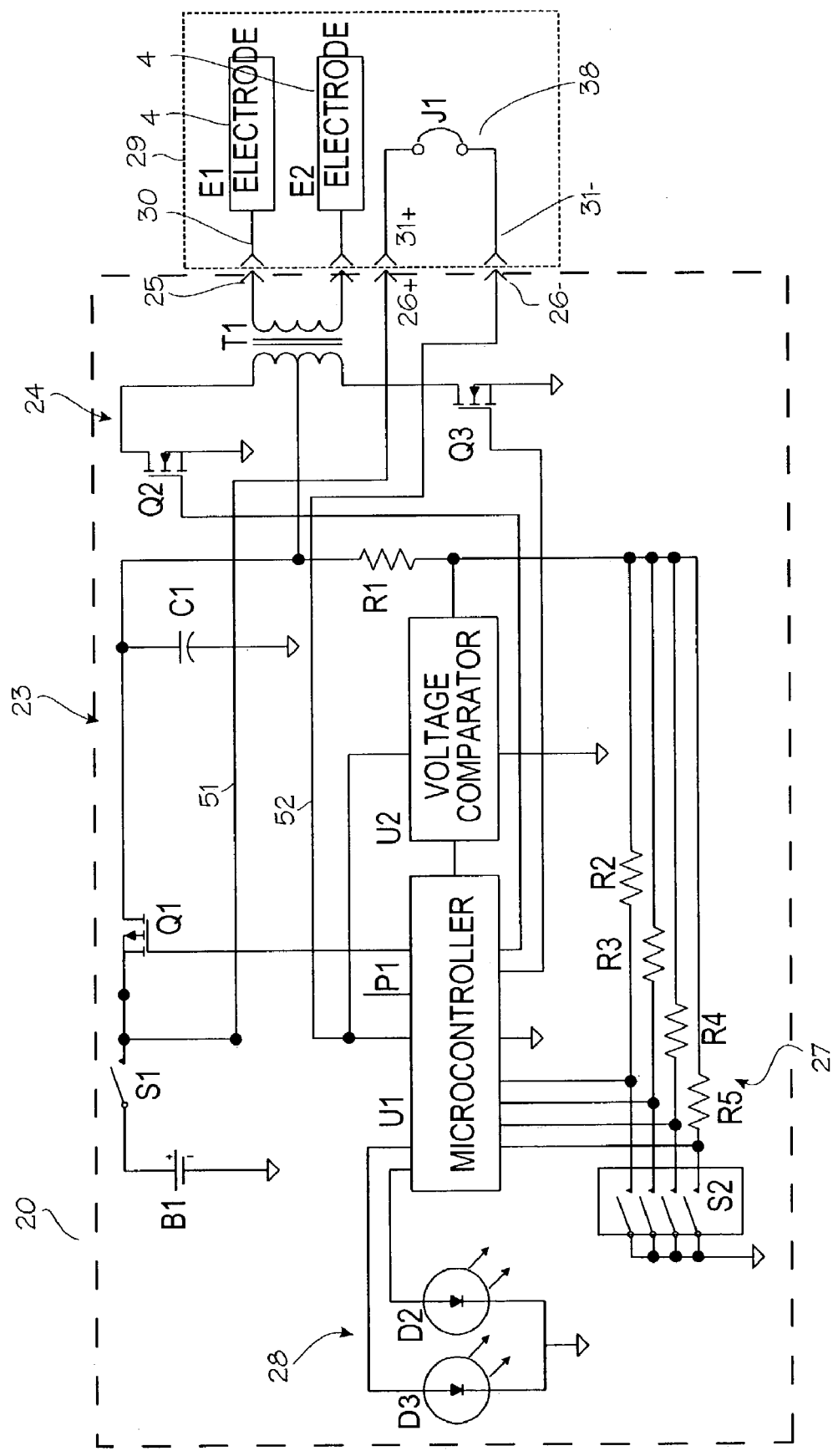
FIG. 13 is a schematic diagram of the circuitry of the system in which the presence of the electrode is required for power operations.

The energy saving embodiment of FIG. 13 operates to prevent battery depletion also. In FIG. 13, the battery supply is located in the base unit and the batteries may be user replaceable. The configuration element may then be a simple jumper J1 that connects a key circuit in the base unit. As shown, the jumper J1 must be in place to connect battery power to the micro-controller through lines 51 and 52. If the jumper is not in place, the micro-controller cannot operate. The jumper may also be used to complete a power-on-reset circuit that "wakes up" the microcontroller. As with a physical keyed mating system, the electronic key may be any component of any value while the key circuit in the base unit is made so that it receives the key and interprets the electronic key or is completed with the electronic key. The key may be supplied separately from the electrode, which may be permanently attached to the base unit. The key is then necessary to operate the device in an operating mode predetermined by the configuration of the key.

Other embodiments are easily developed from the various schematics. One of the configuration states may be assigned to be an Enable/Disable configuration bit for enabling or disabling activation. For example, if two pull-down resistors are used on the microcontroller inputs and pull-up jumpers are used as configuration elements, then the absence of jumpers (indicating that the smart electrode is not attached) produces the null state (00), which is interpreted by the controller as a prohibition against enablement. Any configuration value greater than null indicates that the microcontroller may enable activation. To account for instances where the user attempts to activate the device without the electrode assembly in place, the software can operate to detect the presence of the electrode assembly and if the configuration element is missing, merely go back to "sleep". The user sees a nonfunctioning device, preferably with some indication that the electrode is not in place. When the configuration element is in place, the software on "wake up" would see an appropriate configuration element and would then function normally (including functioning at a specific level or pulse pattern if dictated by a configuration element in the electrode assembly).

In many of the embodiments described above, the electrode assembly includes a component imparting an electronically identifiable parameter to the electrode assembly while the control circuitry, which is operably connected to the electrode through the releasable connectors, is designed to sense the electronically identifiable parameter of the electrode assembly and provide electrical stimulation pulses depending on the value of the sensed electronically identifiable parameter. The stimulation pulses may be provided in differing strength, pulse pattern and duration for different values of the senses parameter, or a single predetermined pulse pattern can be provided or not depending on the presence of the expected component or component value. The electronically identifiable parameter can be resistance of different values, impedance, capacitance, inductance, stored mathematical or logic values in a ROM, or simply open or short circuits. Additionally, while the electrode assembly and base unit have been described in relation to the wrist mounted electro-acupuncture device, the devices and methods described above may be used with therapeutic electrical stimulation devices generally, including TENS units and other such devices.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A device for applying electrical stimulation to a patient having a body having skin, said device comprising:
   a housing having an outer face and an inner face, said inner face being adapted to be applied to the patient;
   an electrode assembly having a releasable connection to the inner face of the housing and adapted for contact with the patient;
   said electrode assembly comprising an electrode and having an electronically identifiable parameter having a value, wherein the electronically identifiable parameter is resistance, said electrode having a coating of an impedance matching film, said impedance matching film positioned so as to be able to come into direct contact with the skin of the patient when the device is applying electrical stimulation to the patient;
   control circuitry operably connected to the electrode, said circuitry being operable to generate electrical stimulation pulses and transmit those pulses through the electrodes to the body of the patient;

said control circuitry being operable to sense the electronically identifiable parameter of the electrode assembly and provide electrical stimulation pulses where the value of the electronically identifiable parameter falls within a predetermined range.

2. A device for applying electrical stimulation to a patient having a body having skin, said device comprising:

a housing having an outer face and an inner face, said inner face being adapted to be applied to the patient;

an electrode assembly releasably attachable to the inner face of the housing and adapted for contact with the patient;

said electrode assembly comprising an electrode and having an electronically identifiable parameter having a value, said electrode having a coating of an impedance matching film, said impedance matching film positioned so as to be able to come into direct contact with the skin of the patient when the device is applying electrical stimulation to the patient;

control circuitry operably connected to the electrode, said circuitry being selectively operable by the patient to generate electrical stimulation pulses and transmit those pulses through the electrodes to the body of the patient;

said control circuitry being operable to sense the electronically identifiable parameter of the electrode assembly and provide electrical stimulation pulses of differing characteristics depending on the value of the sensed electronically identifiable parameter;

wherein the electronically identifiable parameter is resistance; and wherein the control circuitry is operable to provide stimulation pulses having a first set of characteristics where sensed resistance falls within a first predetermined range, and to provide no stimulation where sensed resistance falls within a second predetermined range.

* * * * *